United States Patent [19]

Chowhan

[11] Patent Number: 4,591,592
[45] Date of Patent: May 27, 1986

[54] ACID STABILIZED COMPOSITIONS OF THIENO-PYRIDINE DERIVED COMPOUNDS

[75] Inventor: Zaka-ud-Din T. Chowhan, Sunnyvale, Calif.

[73] Assignee: Syntex (U.S.A.) Inc., Palo Alto, Calif.

[21] Appl. No.: 665,675

[22] Filed: Oct. 29, 1984

Related U.S. Application Data

[60] Division of Ser. No. 376,878, May 10, 1982, Pat. No. 4,490,377, which is a continuation-in-part of Ser. No. 173,310, Jul. 29, 1980, abandoned.

[51] Int. Cl.$^4$ .................. C07D 513/04; A61K 31/435
[52] U.S. Cl. .................................... 514/301; 546/114
[58] Field of Search ......................... 546/114; 514/301

[56] References Cited

U.S. PATENT DOCUMENTS 4,490,377  12/1984  Chowhan ..................... 514/301

OTHER PUBLICATIONS

The Merck Index, Ninth Edition, pp. 300 & 358, Pub. by Merck & Co., Inc. (1976).
Remington Pharmaceutical Sciences, Fourteenth Edition, Mack Pub. Co., pp. 302, 303, 1316, 1317, 1474 and 1475, (1970).
The Merck Index, Ninth Edition, pp. 110-111, (1976).

*Primary Examiner*—Alan L. Rotman
*Attorney, Agent, or Firm*—Charles L. Hartman; Tom M. Moran; Alan M. Krubiner

[57] ABSTRACT

A novel pharmaceutical composition which comprises an acid salt of a thieno-pyridine derived compound, a pharmaceutically acceptable, non-volatile organic acid (particularly citric acid) and optionally other suitable pharmaceutical excipients.

5 Claims, No Drawings

ACID STABILIZED COMPOSITIONS OF THIENO-PYRIDINE DERIVED COMPOUNDS

This is a division of pending U.S. application Ser. No. 376,878 filed May 10, 1982, now U.S. Pat. No. 4,490,377, issued Dec. 25, 1984 which in turn is a continuation-in-part of Ser. No. 173,310, filed July 29, 1980, abandoned.

BACKGROUND OF THE INVENTION

1. Field of the Invention

This invention relates to the stabilization of a pharmaceutical composition containing acid salts of thieno-pyridine derivatives. The stabilization is achieved using a pharmaceutically acceptable, non-volatile organic acid, particularly citric acid.

2. Prior Art

Because of the need to facilitate manufacture, application or consumption of the drug, control of the unit dose, and ease of packaging and handling, drugs are commonly manufactured and marketed in combination with other ingredients of little or no therapeutic value. Against these considerations must be reflected the need to maintain the stability of the composition over the shelf life of the formulation in order to maintain the unit dose and to avoid any untoward effects which may arise from degradation of the drug or excipients.

Initially prepared pills and capsules of compositions containing a thieno-pyridine derived drug named ticlopidine hydrochloride (see U.S. Pat. No. 4,051,141) discolored during normal storage. Analysis of these materials showed degradation of ticlopidine was responsible for the discoloration. The presence of certain excipients such as gelatin, Povidone and magnesium stearate was determined to be the initiating factor in this degradation. In order to market an efficacious and acceptable drug of this structure in the proposed formulation, a means was needed for preventing this degradation which would not interfere with the action of the drug nor have a detrimental or deleterious effect on the user.

No information in the literature deals directly with the prevention of degradation in compositions of thieno-pyridine compounds insofar as is known. Anti-oxidant and chelating additives are available in the chemical arts. However, the selection, where drug formulations are concerned, is limited by the requirement that these additives be pharmaceutically acceptable at levels needed to stabilize compounds in formulations.

One class of anti-oxidant and chelating agent additives for stabilizing organic compounds and compositions is non-volatile organic acids. For example ascorbic acid and citric acid as well as malic acid and tartaric acid have all been used as stabilizers. Citric acid in particular has been used to stabilize fats and oils (U.S. Pat. Nos. 2,197,269 and 3,294,825), hydroquinone solutions (U.S. Pat. No. 3,855,150), and drugs such as fluocinolone acetonide (Great Britain Pat. No. 41034/62), PGE series compounds (German Pat. No. 2,353,797) and L-Dopa formulations (J7 9014-167). None of these references suggest, however, that citric acid or others of that additive class would be useful in stabilizing acid addition salts of thieno-pyridine compounds in solid dosage formulations, such as capsules and tablets.

SUMMARY OF THE INVENTION

It has been discovered that addition of non-volatile, non-toxic acidic compounds having pKa's between 2–6 when added to acid addition salts of thieno-pyridine derived compounds in dry formulations effectively prevented discoloration under normal manufacturing and storage conditions and do not interfere with other consideration of drug efficacy.

Thus one aspect of this invention is a composition containing a pharmaceutically acceptable non-volatile acidic compound having at least one acid functionality and a pharmaceutically acceptable acid addition salt of a thieno-pyridine derived compound chosen from those represented by the formula

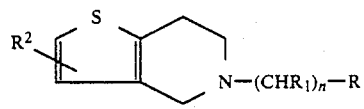

wherein:

R is phenyl or benzyl, each optionally substituted on the phenyl ring with 1 to 3 halogen atoms, alkyl of 1–6 carbon atoms, alkoxy of 1–6 carbon atoms, hydroxy or nitro;

$R_1$ is hydrogen, halogen, hydroxy or alkyl having 1–6 carbon atoms;

$R_2$ is hydrogen or halogen; and n is 1 or 2, and when n is 2, $R_1$ may have different meanings in each $(CHR_1)$ radical. Of particular interest is the compound 5-(2-chlorobenzyl)-4,5,6,7-tetrahydro-thieno[3,2,c]-pyridine HCl (ticlopidine-HCl).

Other pharmaceutically acceptable excipients may be present such as a lubricant, a disintegrant, an extender and a binder.

Another aspect of this invention is a process for preventing degradation of an acid addition salt of formula I type compounds, which process comprises adding a pharmaceutically acceptable non-volatile acidic compound to a dry powder formulation containing one or more said compounds and excipients, for example, a binder, a lubricant, a disintegrant and an extender.

FURTHER DESCRIPTION OF THE INVENTION

The method of practicing this invention may be carried out by developing a formulation for acid addition salts of thioeno-pyridine derived compounds, for example, those of formula I, above, which includes the drug in a pharmaceutically therapeutic amount, a pharmaceutically acceptable non-volatile acidic compound, a lubricant, a binder, a disintegrant, and a diluent. Both tablets and capsules may be prepared from this formulation.

This invention is applicable to any acid salt of a thieno-pyridine derived compound of formula I, above, with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methane sulfonic acid, ethane sulfonic acid, p-toluenesulfonic acid salicylic acid and the like. The hydrochloric acid (HCl) salt is preferred. Generally, a therapeutically effective amount of the acid salt will be that amount necessary to give the desired pharmacological effect, and will constitute about 40–90% by weight per unit formulation. A unit formulation is a pill or capsule containing a therapeutic amount of said drug plus any added excipients.

A pharmaceutically acceptable non-volatile acidic compound is one which is crystalline at room temperature and remains so throughout the range of temperatures normally encountered in the manufacture and storage of pharmaceutical compositions and has a pKa between 2–6. Such a compound may be inorganic or organic. Inorganic compounds would be represented by monobasic sodium phosphate and the like. Representative of organic compounds are ascorbic acid, malic acid, tartaric acid, glycolic acid, malonic acid, malic acid, maleic acid, fumaric acid, benzoic acid, cinnamic acid, mandelic acid, and the like. Of these, citric acid is preferred. Generally, the organic acid is present in an amount of 0.5–5.0% by weight.

A lubricant is generally some fatty acid derived compound or mineral oil which is blended with the formulation to lubricate the punches and die used to form pills and fill capsules. Any lubricant known to the art may be used to practice this invention, for example, magnesium stearate, calcium stearate, stearic acid, lubriwax, mineral oil and the like but magnesium stearate is preferred. A preferred amount is 0.2–3% by dry weight.

One or more binders, in an amount of 1–5% by weight may be chosen from binders generally available such as povidone (polyvinyl pyrrolidinone), starch paste or polymers but povidone is preferred.

A disintegrant, to aid in the breaking up and disintegration of the prepared formulation, is included in this formulation in an amount of 5–15% by dry weight. Any known disintegrant may be used herein but corn starch is preferred.

Choice of a diluent or diluents is at the discretion of the practitioner but, regular lactose is preferred. It is added in the percentage needed to bring the dry powder weight to unity.

The invention is further illustrated by the following examples of the preparation of tablet and pill forms of ticlopidine HCl. These examples are by no means intended to limit the scope of this invention but are given by way of illustration.

EXAMPLE I

| Ingredients | Tablets Grade | Grams Per 20,000 Tab |
| --- | --- | --- |
| Ticlopidine hydrochloride |  | 5,000 g |
| Lactose, regular | USP | 1,747 |
| Povidone (K29-32) | USP | 156 |
| Citric acid anhydrous | USP | 78 |
| Cornstarch | USP | 780 |
| Magnesium stearate | USP | 39 |
| Total wt. |  | 7,800 g |
| Purified water | USP | 1,350 ml |

Tablets are prepared as follows: Ticlopidine hydrochloride and lactose are mixed in a planetary mixer for 10 minutes. Povidone and citric acid are dissolved in 1,350 ml of purified water and added slowly with continuous mixing to the drug/lactose mixture. The resultant wet granulation is mixed for 5 minutes and then passed through a number 4 or number 8 screen. The granulation is dried at 40° C. to between 0.5%–1.5% moisture content and passed through a number 16 screen. The magnesium stearate and corn starch are thoroughly mixed and the mixture is blended with the dried, screened granulation and mixed for 5 minutes. If the moisture content is between 1.5%–2.5%, the granulation is compressed into tablets. As a final step the tablets are given an appropriate coating.

EXAMPLE II

| Ingredient | Capsules Grade | Grams Per 10,000 Caps |
| --- | --- | --- |
| Ticlopidine hydrochloride |  | 2,500 g |
| Lactose, regular | USP | 873.5 |
| Povidone (K29-32) | USP | 78.0 |
| Citric acid anhydrous | USP | 39.0 |
| Cornstarch | USP | 390.0 |
| Magnesium stearate | USP | 19.5 |
| Total wt. |  | 3,900.0 g |
| Purified water | USP | 700 ml |

Capsules are prepared as follows: Ticlopidine hydrochloride and lactose are mixed in a planetary mixer for 10 minutes. Povidone and citric acid are dissolved in 700 ml of purified water and slowly added with continuous mixing to the drug/lactose mixture. Mixing is continued for 5 minutes after addition of the povidone/citric acid solution. The wet granulation is then passed through a number 4 or number 8 screen following which it is dried at 40° C. to 0.5%–1.5% moisture content. This dried granulation is then passed through a number 20 screen. The magnesium stearate and corn starch are mixed and then blended with the dried granulation and mixed for 5 more minutes. The moisture content is then checked to make sure it falls between 1.5%–2.5% moisture, and then 390 milligrams per capsule are transferred into brown, No. 1 opaque gelatin capsules.

Although specific embodiments of the present invention have been described hereinabove it will be evident that various changes in the way of practicing it may be made within the spirit and scope of said invention.

I claim:

1. A stable pharmaceutical composition comprising a therapeutically effective amount of an active ingredient which is a pharmaceutically acceptable acid addition salt (PASS) of a compound having the formula

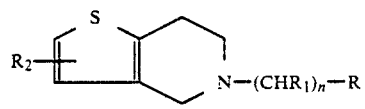

wherein:
R is phenyl or benzyl, each optionally substituted on the phenyl ring with 1 to 3 halogen atoms, alkyl of 1–6 carbon atoms, alkoxy of 1–6 carbon atoms, hydroxy or nitro;
$R_1$ is hydrogen, halogen, hydroxy or alkyl having 1–6 carbon atoms;
$R_2$ is hydrogen or halogen; and
n is 1 or 2, and when n is 2, $R_1$ may have different meanings in each ($CHR_1$) radical and a non-toxic stabilizing amount of a pharmaceutically, non-volatile acidic compound which is ascorbic acid, benzoic acid, citric acid, fumaric acid, or tartaric acid and at least one pharmaceutically acceptable excipient.

2. The composition of claim 1 wherein said acidic compound is present in an amount of 0.5-5.0% (w/w) relative to the active ingredient.

3. The composition of claim 3 wherein said compound is the hydrochloride salt of 5-(2-chlorobenzyl)-4,5,6,7-tetrahydrothieno[3,2-c]pyridine said acid is citric acid and is present in an amount of 1-1.5% (w/w).

4. A pharmaceutical composition which comprises
- 40-90% by weight of a pharmaceutically acceptable acid addition salt of a thieno-pyridine derived compound;
- 0.5-5% by weight of a pharmaceutically acceptable, non-volatile organic acid which is ascorbic acid, benzoic acid, citric acid, fumaric acid, or tartaric acid;
- 0.2-5% by weight of a pharmaceutically acceptable lubricant;
- 5-15% by weight of a pharmaceutically acceptable disintegrant;
- 1-5% by weight of a pharmaceutically acceptable binder and the remainder a pharmaceutically acceptable diluent.

5. The composition of claim 4 wherein the compound is the hydrochloride salt of 5-(2-chlorobenzyl)-4,5,6,7-tetrahydrothieno[3,2-c]pyridine, said acid is citric acid, and said lubricant is magnesium stearate.

* * * * *